(12) United States Patent
Raksi et al.

(10) Patent No.: US 9,301,878 B2
(45) Date of Patent: *Apr. 5, 2016

(54) ADAPTIVE PATIENT INTERFACE

(71) Applicant: Alcon LenSx, Inc., Aliso Viejo, CA (US)

(72) Inventors: Ferenc Raksi, Mission Viejo, CA (US); Tibor Juhasz, Corona del Mar, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/338,181

(22) Filed: Jul. 22, 2014

(65) Prior Publication Data

US 2014/0330259 A1    Nov. 6, 2014

Related U.S. Application Data

(63) Continuation of application No. 12/824,107, filed on Jun. 25, 2010, now Pat. No. 8,845,624.

(51) Int. Cl.
*A61B 18/18* (2006.01)
*A61F 9/009* (2006.01)

(52) U.S. Cl.
CPC ..................... *A61F 9/009* (2013.01)

(58) Field of Classification Search
CPC .................. A61F 9/008; A61F 9/009
USPC .......................................... 606/4–6
See application file for complete search history.

(56) References Cited

U.S. PATENT DOCUMENTS

| | | | |
|---|---|---|---|
| 3,706,304 A | 12/1972 | Sisler | 600/489 |
| 4,367,018 A | 1/1983 | Abe | |
| 4,453,546 A | 6/1984 | Katz et al. | |
| 4,600,008 A | 7/1986 | Schmidt | |

(Continued)

FOREIGN PATENT DOCUMENTS

| | | |
|---|---|---|
| CA | 2128104 A1 | 7/1993 |
| EP | 0627207 | 12/1994 |

(Continued)

OTHER PUBLICATIONS

European extended Search Report for European Application No. 11798943 with mailing date Sep. 27, 2013, 5 pages.

(Continued)

*Primary Examiner* — William Thomson
*Assistant Examiner* — John R Downey
(74) *Attorney, Agent, or Firm* — S. Brannon Latimer

(57) ABSTRACT

A patient interface for an ophthalmic system can include an attachment module, attachable to the ophthalmic system, and a contact module, configured to accommodate a viscoelastic substance between the patient interface and a procedure eye. The viscoelastic substance can include a fluid, a liquid, a gel, a cream, an artificial tear, a film, an elastic material, or a viscous material. The refractive index of the viscoelastic substance can be within a range of approximately 1.24-1.52 at an operating wavelength of the ophthalmic system. The patient interface can further include input ports, output ports, and a suction system. It can be an integrated design or a multi-piece patient interface. The viscoelastic substance can be provided by injection, on the cornea, at the contact module, or in a space bounded by soft elastic films or membranes, such as in a bag.

20 Claims, 15 Drawing Sheets

(56) References Cited

U.S. PATENT DOCUMENTS

| | | | |
|---|---|---|---|
| 4,718,418 A | 1/1988 | L'Esperance, Jr. | |
| 4,753,526 A | 6/1988 | Koester | |
| 4,905,711 A | 3/1990 | Bennett et al. | |
| 4,907,586 A | 3/1990 | Bille et al. | |
| 4,941,871 A | 7/1990 | Ward | |
| 4,964,717 A | 10/1990 | Koester | |
| 4,994,058 A | 2/1991 | Raven et al. | |
| 5,108,412 A | 4/1992 | Krumeich et al. | |
| 5,112,328 A | 5/1992 | Taboada et al. | |
| 5,196,027 A | 3/1993 | Thompson et al. | 128/898 |
| 5,209,720 A | 5/1993 | Unger | |
| 5,226,903 A | 7/1993 | Mizuno | |
| 5,252,998 A | 10/1993 | Reis et al. | |
| 5,280,491 A | 1/1994 | Lai | |
| 5,311,224 A | 5/1994 | Enomoto | |
| 5,324,281 A | 6/1994 | Muller | |
| 5,336,215 A | 8/1994 | Hsueh et al. | |
| 5,360,424 A | 11/1994 | Klopotek | |
| 5,364,390 A | 11/1994 | Taboada et al. | |
| 5,423,801 A | 6/1995 | Marshall et al. | |
| 5,450,144 A | 9/1995 | Ben Nun | |
| 5,549,632 A | 8/1996 | Lai | 606/5 |
| 5,656,186 A | 8/1997 | Mourou et al. | |
| 5,861,955 A | 1/1999 | Gordon | 356/511 |
| 5,871,772 A | 2/1999 | Cantoro | 424/427 |
| 5,957,832 A | 9/1999 | Taylor et al. | |
| 6,019,472 A | 2/2000 | Koester et al. | 351/219 |
| 6,090,100 A | 7/2000 | Hohla | |
| 6,099,541 A | 8/2000 | Klopotek | 606/166 |
| 6,143,010 A | 11/2000 | Silvestrini et al. | |
| 6,210,401 B1 | 4/2001 | Lai | |
| 6,254,595 B1 | 7/2001 | Juhasz et al. | |
| 6,342,053 B1 | 1/2002 | Berry | |
| 6,344,040 B1 | 2/2002 | Juhasz et al. | |
| 6,373,571 B1 | 4/2002 | Juhasz et al. | |
| 6,412,334 B1 | 7/2002 | Kral et al. | |
| 6,436,113 B1 | 8/2002 | Burba et al. | |
| 6,451,006 B1 | 9/2002 | Bille | |
| 6,458,141 B1 | 10/2002 | Peyman | |
| 6,579,282 B2 | 6/2003 | Bille et al. | |
| 6,623,476 B2 | 9/2003 | Juhasz et al. | |
| 6,634,753 B1 | 10/2003 | Rozenman | |
| 6,641,577 B2 | 11/2003 | Bille | |
| 6,676,653 B2 | 1/2004 | Juhasz et al. | |
| 6,730,073 B2 | 5/2004 | Bruce | |
| 6,730,074 B2 | 5/2004 | Bille et al. | |
| 6,733,491 B2 | 5/2004 | Kadziauskas et al. | |
| 6,752,778 B1 | 6/2004 | Fiedler et al. | 604/23 |
| 6,776,824 B2 | 8/2004 | Wen | |
| 6,780,176 B2 | 8/2004 | Hasegawa | 606/27 |
| 6,863,667 B2 | 3/2005 | Webb et al. | |
| 6,899,707 B2 | 5/2005 | Scholler et al. | |
| 6,905,641 B2 | 6/2005 | Platt et al. | 264/1.38 |
| 6,991,629 B1 | 1/2006 | Juhasz et al. | |
| 7,018,376 B2 | 3/2006 | Webb et al. | |
| 7,125,119 B2 | 10/2006 | Farberov | |
| 7,238,176 B2 | 7/2007 | Loesel et al. | |
| 7,244,026 B1 | 7/2007 | Ross, III et al. | |
| 7,285,096 B2 | 10/2007 | Burba et al. | 600/459 |
| 7,330,275 B2 | 2/2008 | Raksi | |
| 7,371,230 B2 | 5/2008 | Webb et al. | |
| 7,390,089 B2 | 6/2008 | Loesel et al. | |
| 7,402,159 B2 | 7/2008 | Loesel et al. | |
| 7,452,080 B2 | 11/2008 | Wiltberger et al. | |
| 7,452,081 B2 | 11/2008 | Wiltberger et al. | |
| 7,595,077 B2 | 9/2009 | Wakamatsu et al. | |
| 7,611,507 B2 | 11/2009 | Raksi et al. | |
| 8,070,290 B2 | 12/2011 | Gille et al. | 351/219 |
| 8,444,579 B2 | 5/2013 | Silwa | |
| 8,600,723 B2 | 12/2013 | Parker et al. | |
| 2001/0021844 A1 | 9/2001 | Kurtz et al. | |
| 2002/0103481 A1 | 8/2002 | Webb et al. | |
| 2002/0103482 A1 | 8/2002 | Scholler et al. | |
| 2003/0153904 A1 | 8/2003 | Patel | |
| 2004/0036839 A1 | 2/2004 | Fischer et al. | |
| 2004/0070761 A1 | 4/2004 | Horvath et al. | |
| 2004/0254568 A1 | 12/2004 | Rathjen | |
| 2005/0143718 A1 | 6/2005 | Rathjen | |
| 2005/0154408 A1 | 7/2005 | Dybbs | 606/166 |
| 2006/0179992 A1 | 8/2006 | Kermani | |
| 2006/0195078 A1 | 8/2006 | Webb et al. | |
| 2006/0261502 A1 | 11/2006 | Platt et al. | 264/1.32 |
| 2007/0093795 A1 | 4/2007 | Melcher et al. | |
| 2007/0093796 A1 | 4/2007 | Raksi et al. | |
| 2007/0173791 A1 | 7/2007 | Raksi | |
| 2007/0253083 A1 | 11/2007 | Muhlhoff et al. | |
| 2008/0071254 A1 | 3/2008 | Lummis et al. | |
| 2008/0194915 A1 | 8/2008 | Blackhurst et al. | |
| 2009/0069794 A1 | 3/2009 | Kurtz | |
| 2009/0137989 A1 | 5/2009 | Kataoka | |
| 2009/0182310 A1 | 7/2009 | Gertner et al. | |
| 2010/0022994 A1 | 1/2010 | Frey et al. | |
| 2010/0274228 A1 | 10/2010 | Mrochen et al. | 604/541 |
| 2011/0022035 A1 | 1/2011 | Porter et al. | 606/4 |
| 2011/0166535 A1 | 7/2011 | Hasegawa et al. | 604/294 |
| 2011/0190739 A1 | 8/2011 | Frey et al. | |

FOREIGN PATENT DOCUMENTS

| | | |
|---|---|---|
| EP | 0536951 B1 | 8/1997 |
| EP | 0634947 B1 | 12/2001 |
| EP | 1982640 | 10/2008 |
| WO | 88-03396 | 5/1988 |
| WO | 89-06519 | 7/1989 |
| WO | 2008/112292 | 9/2008 |

OTHER PUBLICATIONS

European Supplementary Search Report for European Application No. 08799433.1 with mailing date Feb. 13, 2013, 6 pages.

International Written Opinion for corresponding International Application No. PCT/US2012/036546 with mailing date Sep. 5, 2012, 3 pages.

International Search Report for corresponding International Application No. PCT/US2012/049319 with mailing date Nov. 19, 2012, 4 pages.

International Search Report for corresponding International Application No. PCT/US2012/052460 with mailing date Dec. 11, 2012, 6 pages.

International Search Report dated Feb. 29, 2012 for corresponding International Application No. PCT/ US2011/041676, 3 pages.

Chinn, S.R., et al., "Optical coherence tomography using a frequency-tunable optical source," *Optics Letters*, 22(5):340-342, Mar. 1997, 3 pages.

Huber, R., et al., "Three-dimensional and C-mode OCT imaging with a compact, frequency swept laser source at 1300 nm," *Optics Express*, 13(26):10523-10538, Dec. 2005, 16 pages.

Yun, S.H., et al., "Wavelength-swept fiber laser with frequency shifted feedback and resonantly swept intra-cavity acoustooptic tunable filter," *IEEE Journal of Selected Topics in Quantum Electronics*, 3(4):1087-1096, Aug. 1997, 10 pages.

International Search Report and Written Opinion dated Mar. 19, 2009 for International Application No. PCT/US2008/075902, filed Sep. 10, 2008, 6 pages.

ADAPTIVE PATIENT INTERFACE

CROSS REFERENCE TO RELATED APPLICATION

This patent document is a continuation of, and thus claims benefit of and priority from co-pending U.S. patent application Ser. No. 12/824,107, entitled "Adaptive Patient Interface", by Ferenc Raksi and Tibor Juhasz, filed on Jun. 25, 2010, incorporated herein in its entirety by reference as part of the specification of the present patent document.

BACKGROUND

1. Field of Invention

This patent document relates to patient interfaces that attach an ophthalmic system to an eye for anterior segment eye procedures. More particularly, this patent document relates to adaptive patient interfaces that reduce a deformation of a cornea of the procedure eye.

2. Description of Related Art

This patent document describes examples and embodiments of techniques and devices for securing an ophthalmic system to an eye to perform an anterior segment eye procedure. These devices are often referred to as patient interfaces. Since patient interfaces serve to connect the ophthalmic system and the eye of the patient, their performance is an important contribution to the precision and success of the ophthalmic procedures. Thus, improvements in patient interfaces can lead to improvements in the precision and reliability of ophthalmic procedures.

SUMMARY

Briefly and generally, a patient interface for an ophthalmic system can include an attachment module, attachable to the ophthalmic system; and a contact module, configured to accommodate a viscoelastic substance between the patient interface and a procedure eye.

In some implementations, the viscoelastic substance can include a fluid, a liquid, a gel, a cream, an artificial tear, a film, an elastic material, or a viscous material.

In some implementations, a refractive index of the viscoelastic substance is closer to a refractive index of a cornea of the procedure eye than to a refractive index of air at an operating wavelength of the ophthalmic system.

In some implementations, a refractive index of the viscoelastic substance is within a range of approximately 1.24-1.52 at an operating wavelength of the ophthalmic system.

In some implementations, a refractive index of the viscoelastic substance is within a range of approximately 1.35-1.41 at an operating wavelength of the ophthalmic system.

In some implementations, the attachment module and the contact module are separate and connectable.

In some implementations, the attachment module and the contact module are integrated components of the patient interface.

In some implementations, a component of the patient interface is at least one of disposable, sterilizable, and reusable.

Some implementations can include one or more input ports to introduce the viscoelastic substance into an accommodation space at least partially defined by the contact module.

Some implementations can include one or more output openings configured to enable a discharge of air, gas, or the viscoelastic substance from the contact module.

In some implementations, the one or more output openings can include a vent port, configured to keep a pressure in an accommodation space at least partially defined by the contact module at approximately ambient pressure.

Some implementations can include a suction subsystem configured to at least partially immobilize the procedure eye for an ophthalmic procedure.

In some implementations, the suction subsystem is arranged in relation to the contact module; and the suction subsystem is connectable to a vacuum suction system to create a partial vacuum between the suction subsystem and the procedure eye.

In some implementations, the patient interface is configured to keep a change of an apical curvature of a cornea of the procedure eye below 10% upon an attachment of the patient interface to the procedure eye.

In some implementations, the patient interface is configured to keep a change of the apical curvature of the cornea of the procedure eye below 3% upon the attachment of the patient interface to the procedure eye.

In some implementations, the ophthalmic system can include at least one of an imaging system, a diagnostic system, a laser system, and an ophthalmic surgical system.

In some implementations, the contact module is configured to accommodate the viscoelastic substance before being attached to the procedure eye.

In some implementations, the contact module is configured to accommodate the viscoelastic substance after the viscoelastic substance has been applied to the procedure eye.

In some implementations, the contact module can include a soft elastic film or membrane, configured to contain the viscoelastic substance in an accommodation space at least partially defined by the contact module, and to form a soft and elastic contact surface for the procedure eye.

Some implementations can include a soft bag, containing the viscoelastic substance.

In some implementations, the patient interface can be connectable to a degassing subsystem, configured to degas the viscoelastic substance.

In some implementations, a patient interface for an ophthalmic system can include a contact module, configured to be attachable to a first eye with an apical corneal radius of R1 and separately to a second eye with an apical corneal radius of R2; and to limit a change of each apical corneal radius to less than 0.5*|R1-R2| when the contact module is attached to the first eye and separately to the second eye, wherein the apical corneal radii R1 and R2 are between 7.5 mm and 8.2 mm.

In some implementations, the contact module can be configured to limit the change of each apical corneal radius to less than 0.25*|R1-R2| when the contact module is attached to the eyes.

Some implementations can include an attachment module attachable to the ophthalmic system, wherein the attachment module and the contact module can be either separate and connectable, or integrated components of the patient interface.

Some implementations can include one or more fluid ports, configured to introduce a fluid or gel into a containment space at least partially defined by the procedure eye and the patient interface.

Some implementations can include one or more output ports, configured to enable a discharge of at least one of air, fluid or gel from a containment space at least partially defined by the patient interface and the procedure eye.

Some implementations can include a suction port, configured to enable a creation of a partial vacuum between a portion of the patient interface and a portion of the procedure eye.

Some implementations can include a distal lens, wherein the distal lens does not contact a cornea of the procedure eye after an attachment of the patient interface to the procedure eye.

Some implementations can include a soft layer, configured to contain a viscoelastic substance, and to provide a soft contact surface for a procedure eye.

In some implementations, a method of utilizing a patient interface for an ophthalmic procedure can include applying the patient interface to a procedure eye in preparation for the ophthalmic procedure; and providing a viscoelastic substance to at least one of a cornea of the procedure eye and a contact portion of the patient interface, wherein the providing is performed before, during or after the applying.

In some implementations, providing the viscoelastic substance can include providing a fluid, a liquid, a gel, a cream, an artificial tear, a film, an elastic material, or a viscous material.

In some implementations the providing can include introducing the viscoelastic substance through an input port of the patient interface into a contact space, at least partially bordered by the patient interface and the procedure eye after the applying.

In some implementations the providing can include introducing the viscoelastic substance onto the cornea of the procedure eye before the applying.

In some implementations the providing can include providing the viscoelastic substance at the contact portion of the patient interface before the applying.

In some implementations the providing can include providing the viscoelastic substance in a space at least partially defined by one or more soft films or membranes.

In some implementations the providing can include using a syringe to introduce the viscoelastic substance.

In some implementations the ophthalmic procedure can include at least one of an imaging procedure, a diagnostic procedure, a laser-assisted procedure, and an ophthalmic surgical procedure.

Some implementations can include degassing the viscoelastic substance.

In some implementations the degassing can include at least one of reducing a pressure, heating, performing membrane degasification, substituting an inert gas, and adding a reductant.

DETAILED DESCRIPTION

Figure 1A:
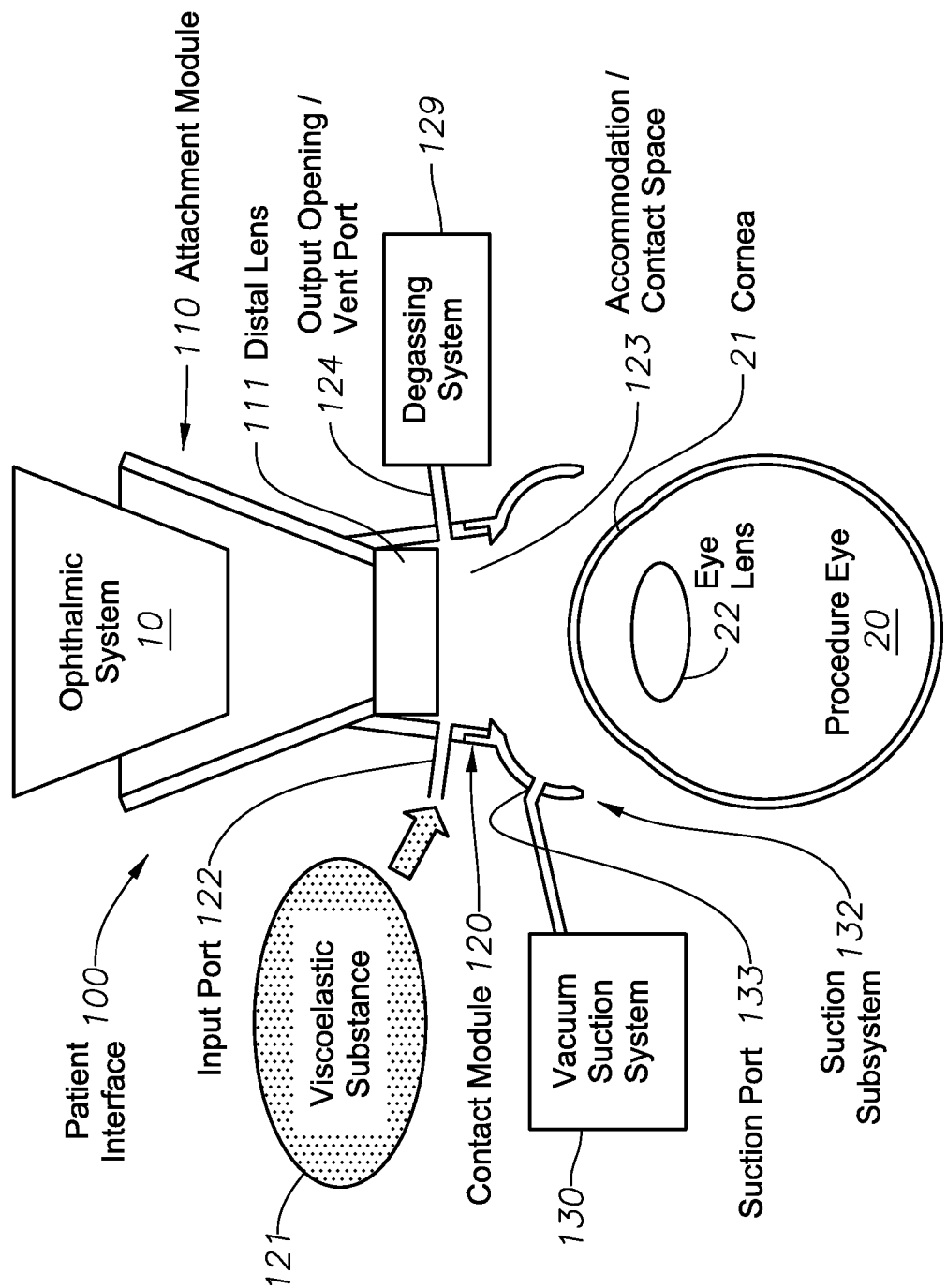
FIG. 1A illustrates an integrated patient interface 100.

Some laser eye surgical procedures, such as corneal refractive corrections and laser-assisted lens capsulotomies, may benefit from immobilizing the procedure eye relative to the surgical laser system during the procedure. Some systems include a so-called patient interface to carry out this task. One end of the patient interface can be attached to the distal end of the surgical laser system. The other end can include a contact lens pressed against the procedure eye. Such patient interfaces hold the eye steady relative to the surgical laser, enabling a high precision directing and focusing of the laser beam to a predetermined target location of the eye. Some patient interfaces can also be used to provide a reference surface for the targeting of the laser so that its focus depth can be defined relative to the contact lens.

Some patient interfaces use flat contact "lenses", also called applanation plates. Others include curved contact lenses. In operation, either of these contact lenses can be pressed against the cornea of the eye, essentially immobilizing the eye and forcing the cornea to conform to the contact surface of the contact lens. To overcome the slipperiness of the tear film covering the eye, the contact lenses are typically held in place by a vacuum system, such as a suction ring.

While using rigid contact lenses has the benefit of providing a well-defined optical element for optimizing the beam properties of the laser, and possibly of providing a reference plane to direct the surgical laser with precision, there are also disadvantages associated with forcing rigid lenses against the procedure eye.

One of the problems is that upon docking to the eye, the contact lens typically deforms the cornea, as their curvatures are generally different from each other. This change of corneal curvature can cause internal deformations since the support system of the lens of the eye is very soft. Therefore, the docking of a rigid patient interface typically shifts and tilts the lens relative to the optical axis of the eye. This displacement and tilt may make the cuts of a typical cataract surgery, the circular capsulotomy cut on the capsular bag and the cataract surgical pattern cut in the lens itself, off-center and distorted, leading to a deterioration of the optical outcome of the cataract procedure.

Altering the cornea's natural curvature may also produce wrinkles on the surface of the cornea that could distort the laser beam. This distortion can lead to increased scattering and astigmatism of the beam, possibly requiring the use of a higher energy laser beam. The distortion can also lead to a loss of precision of the directing the laser beam.

The corneal deformation can be reduced by designing the contact lens to have a curvature equaling that of a typical cornea. However, since corneal radii vary considerably from patient to patient, even these patient interfaces deform the corneas of most patients.

To address these problems, some implementations of the present invention may use a patient interface whose lens does not make direct contact with the cornea. Such an embodiment can successfully minimize the corneal deformation, reducing the aforementioned problems, possibly even avoiding them altogether.

However, such non-contact designs may have their own challenges as (1) the light propagating through an air gap before entering the cornea may reduce the beam quality by increasing its astigmatism, for example; (2) the surface of the cornea can dry out quickly, increasing the light scattering at the corneal surface considerably; and (3) the surgical eye may have an excessive amount of movement because the patient interface does not hold it steady by direct contact.

Implementations of the present invention include patient interfaces that reduce the corneal deformation because their lenses do not make direct contact with the cornea, while at the same time offer solutions for the above three challenges.

FIG. 1A illustrates an implementation of a patient interface, or PI, 100. The PI 100 can include an attachment module 110 and a contact module 120. A function of the attachment module 100 can be to attach the PI 100 to an ophthalmic system 10. In some embodiments the attachment module 110 can be connected to a distal end, application tip, or objective of the ophthalmic system 10. A function of the contact module 120 can be to form a connection to an eye 20 on which an ophthalmic procedure is performed. This eye will be sometimes referred to as the procedure eye 20.

The ophthalmic system 10 can include an imaging system, a diagnostic system, a laser system or an ophthalmic surgical system.

The PI 100 can include a distal lens, or non-contact lens 111. The distal lens 111 can be the last refractive element of the optical train of the ophthalmic system 10. The distal lens 111 can be a flat applanation plate or a lens with one or both surfaces curved. Its role can be similar to that of the contact lens of other patient interfaces, with the difference that in various embodiments the distal lens 111 does not contact a cornea 21 of the eye 20. For this reason, the distal lens 111 does not deform the cornea 21, thus avoiding the displacement and tilt of lens 22, and the wrinkling of the cornea 21.

Figure 1B:
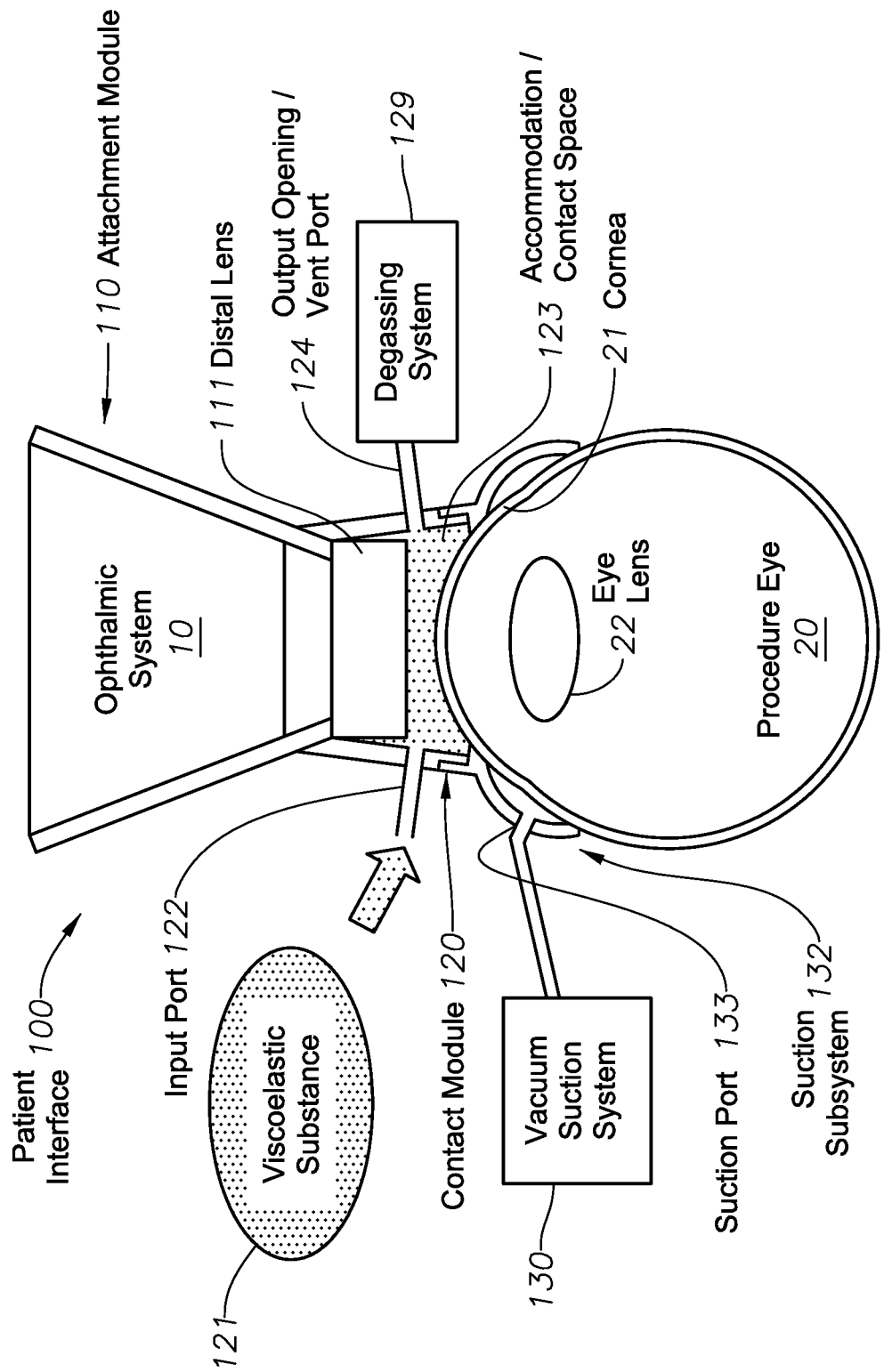
FIG. 1B illustrates the patient interface 100 attached to the ophthalmic system 10 and the procedure eye 20.

FIG. 1B illustrates the PI 100 after it has been connected or docked to the eye 20. Visibly, in this implementation the distal lens or non-contact lens 111 is indeed not in direct contact with the cornea 21 of the eye 20. Because of this lack of contact, the PI 100 minimizes the deformation of the eye.

A measure of the deformation is the relative change of an apical curvature of the cornea of the procedure eye when the patient interface is attached to the procedure eye. Some embodiments of the PI 100 keep the change of the apical curvature of the cornea below 10% when the PI is attached to the eye. In other embodiments, the relative change of the apical corneal curvature can be kept below 3%.

Referring to FIG. 1A, the contact module 120 can be formed to accommodate a viscoelastic substance 121 in a space between the PI 100 and the cornea 21. This design can address the above challenge (1), since when the viscoelastic substance 121 fills up the space between the distal lens 111 and the cornea 21, the laser beam or light of the ophthalmic system 10 does not propagate through air.

When there is an air gap between the distal lens 111 and the cornea of the procedure eye 20, the surgical or diagnostic light beams are refracted at the posterior surface of the distal lens 111 and at the anterior corneal surface. This latter refraction is proportional to (n(a)-n(c)), the difference between the refractive index n(a) of the air, and n(c), that of the cornea.

The deterioration of the beam quality can be reduced by filling up the air gap with the viscoelastic substance 121 between the patient interface 100 and the cornea 21. In this case, the beam refraction and astigmatism will be proportional to (n(v)-n(c)), where n(v) is an index of refraction of the viscoelastic substance 121.

Thus, in some embodiments the viscoelastic substance 121 can be chosen to have a refractive index n(v) closer to n(c), the refractive index of the cornea, than to n(a), the refractive index of air, at an operating wavelength of the ophthalmic system 10. Since an index of refraction of the cornea is typically close to n(c)=1.38, in some embodiments this translates to the viscoelastic substance 121 having an index of refraction n(v) in the approximate range of 1.24-1.52. In other embodiments, n(v) can fall in the approximate range of 1.35-1.41.

Introducing the viscoelastic substance 121 to fill the space between the distal lens 111 of the patient interface and the cornea 21 also resolves challenge (2) as the cornea is not exposed to air in this design. Rather, the corneal surface can remain wetted by the viscoelastic substance 121, preventing the cornea 21 from drying out.

In various implementations, the viscoelastic substance 121 can be one of a wide variety of substances, including a fluid, a liquid, a gel, a cream, an artificial tear, a film, an elastic material, or a viscous material. In some cases, two or more of these substances can be present in the viscoelastic substance 121.

The viscoelastic substance 121 can be inserted through an input port 122 into an accommodation space 123. The accommodation space 123 can have numerous different embodiments: it can be a concave space at least partially defined by the contact module 120 and the distal lens 111, or it can be any recessed chamber of the patient interface 100. It can be also defined by a combination of the contact module 120, the distal lens 111 and the accommodation module 110.

FIG. 1B illustrates that phase of the operation of the PI 100 when the PI 100 has been docked to the eye and the viscoelastic substance has been introduced into the accommodation space 123 through the input port 122, essentially filling up the space or air gap between the distal lens and the cornea.

Implementations of the PI 100 can include an output opening or vent port 124. The vent port 124 can have several functions, including discharging the air, displaced by the viscoelastic substance 121, from the accommodation space 123. Also, the viscoelastic substance 121 itself can be discharged from the accommodation space 123 through this vent port 124, thus accelerating its introduction into the accommodation space 123. Doing so also increases the homogeneity of the spatial distribution of the viscoelastic substance 121.

Further, the vent port 124 can be configured to keep a pressure in the accommodation space 123 close to the ambient pressure. This functionality can reduce or prevent unintended gas seepage across the contact module 120. The vent port 124 can be also used to degas the introduced viscoelastic substance 121, as described below in more detail.

In various embodiments, there can be more than one input ports 122 and more than one output openings 124.

A vacuum suction system 130 can be attached to a suction subsystem 132 through a suction port 133 in some embodiments. The suction subsystem 132 can be configured to at least partially immobilize the procedure eye 20 for an ophthalmic procedure. An example of the suction subsystem 132 is a suction ring formed as part of the contact module 120. The suction ring 132 can include a skirt or vacuum seal formed to make an airtight contact with the eye. Applying suction through the suction port 133 can keep the eye steady.

Several different types of the suction subsystem 132 are known. The aforementioned suction ring is one of them, where the partial vacuum acts on a ring around the cornea. In other implementations the partial vacuum can be applied to larger portions of the accommodation space 123. More than one suction chamber can also be formed.

In the implementation of FIG. 1A-B, the attachment module 110 and the contact module 120 are components of a one-piece, integrated patient interface 100. An aspect of this integrated PI 100 is that sometimes the precise aligning and docking of the PI 100 to the procedure eye 20 can be time consuming, as it can require the adjustment of a portion of the ophthalmic system 10. This movement can involve moving a gantry or an articulated arm of the ophthalmic system 10 that contains lenses and mirrors. Therefore, this movement can require more complex technical solutions.

Figure 2A:
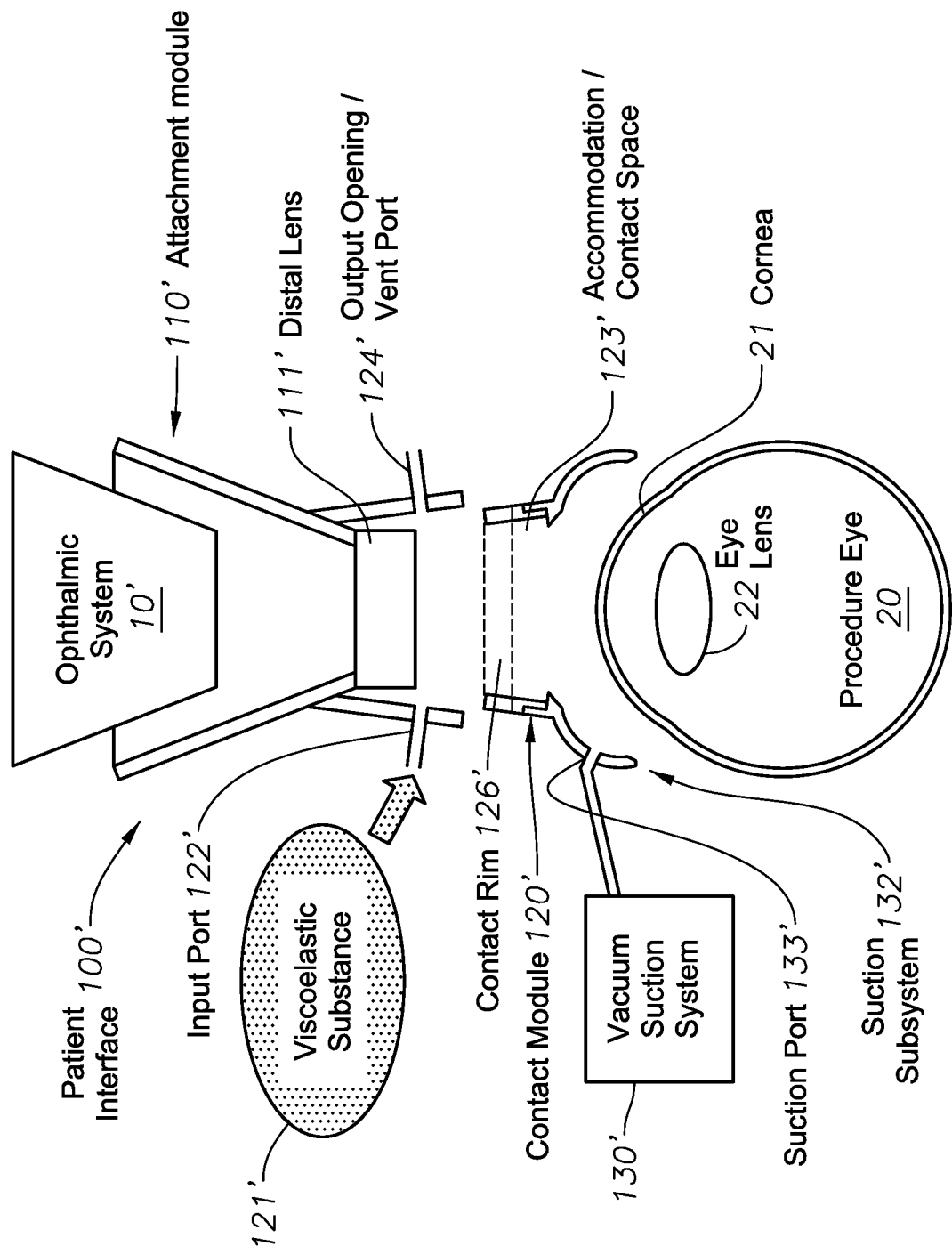
FIG. 2A-B illustrate a two-piece patient interface 100'.

FIG. 2A illustrates another embodiment of a patient interface 100' that improves the efficiency of the docking of the PI 100' and simplifies its technology. The PI 100' achieves these features by having a separate attachment module 110' and a separate contact module 120'.

The attachment module 110' can be attached to the distal end of the ophthalmic system 10 or 10', such as to its objective, with ease, as this step does not require aligning the ophthalmic system with the eye. The separate contact module 120' can include a so-called gripper (not shown). A variety of the presently known grippers can be combined with the contact module 120' to provide improved control and ease of manipulations for the operator of the system. The contact module 120' is also relatively easy to dock to the eye as moving and adjusting it does not require moving an articulated arm of the ophthalmic system 10'.

Figure 2B:
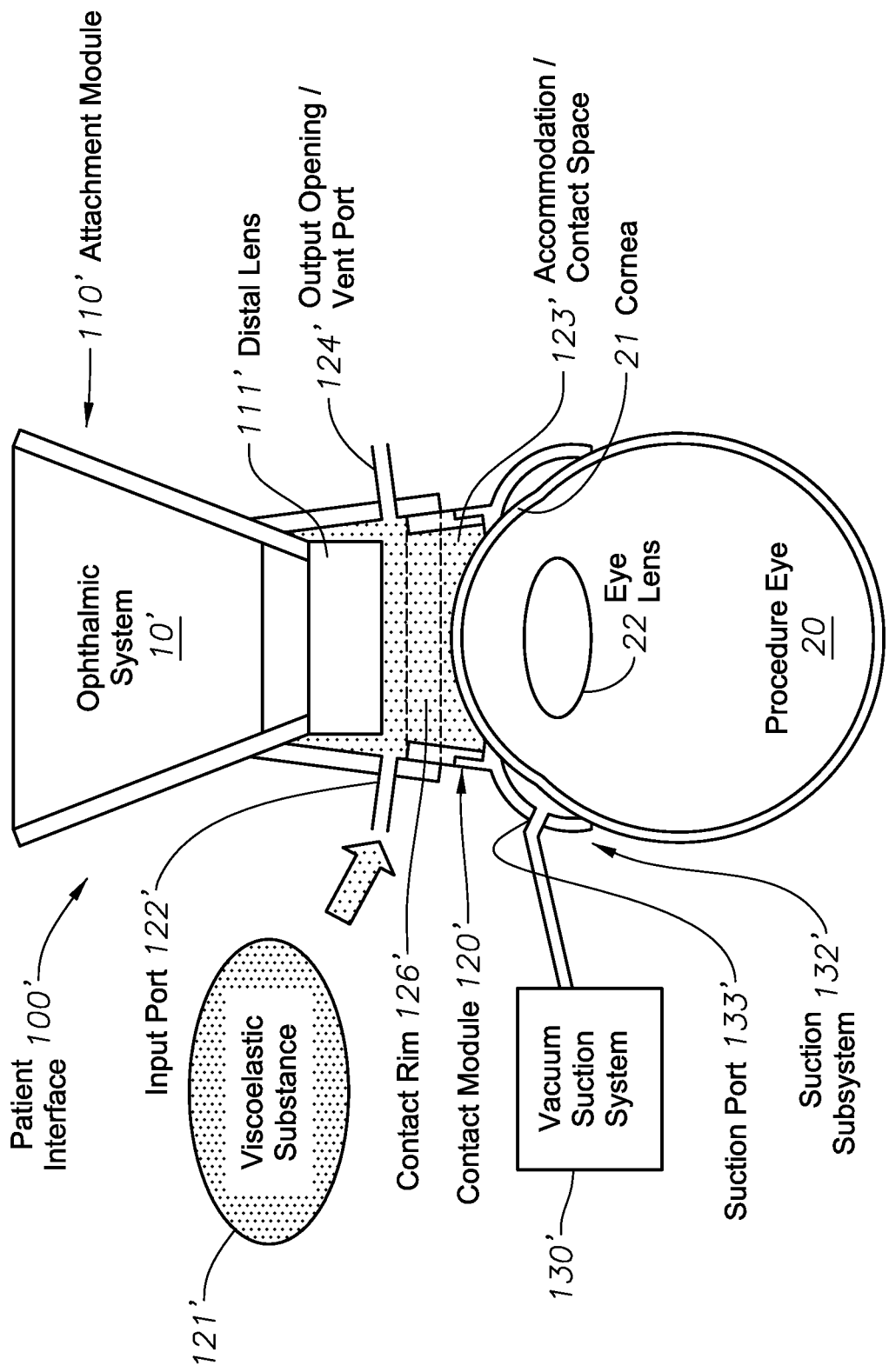

FIG. 2B illustrates that once the attachment module 110' is attached to the ophthalmic system 10' and the contact module 120' is docked to the eye, an operator of the system, such as a surgeon, can gently move the gripper to align the contact module 120' with the attachment module 110'. When an alignment is achieved in the x-y directions, the attachment module 110' can be gently lowered onto the contact module 120' to complete a connection at a contact rim 126', completing the patient interface 100'. Once a sufficient seal has been established, a viscoelastic substance 121' can be provided through an input port 122' into an accommodation space 123', at least partially defined by the PI 100' and the cornea 21.

Most of the elements of the PI 100' are analogous to the corresponding elements of PI 100 and are labeled accordingly. Thus, their earlier description is not repeated here.

In the embodiment of FIGS. 2A-B of the PI 100', a distal lens 111' can be part of the attachment module 110'.

Figure 3:
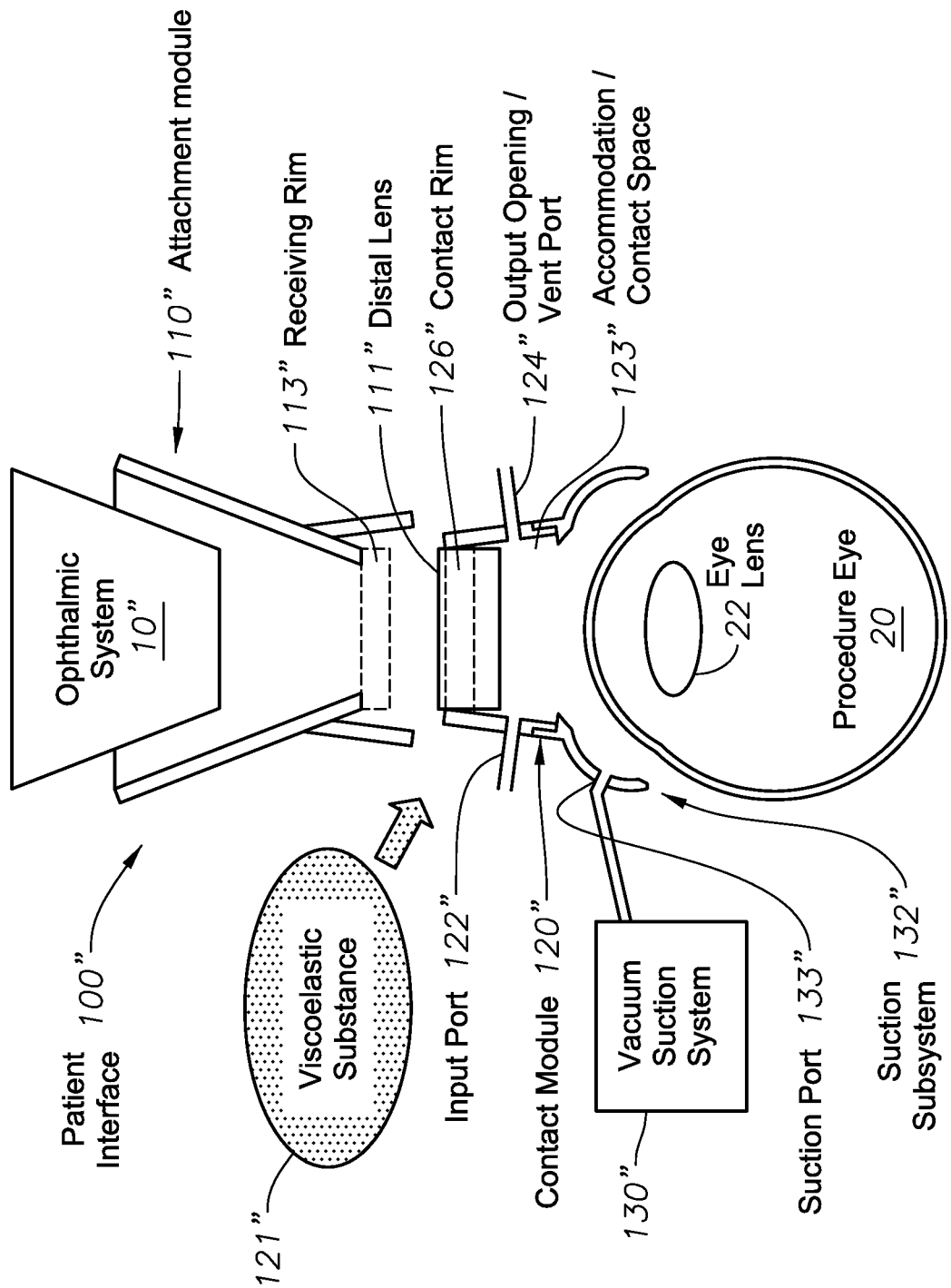
FIG. 3 illustrates another embodiment of a two-piece patient interface 100".

FIG. 3 illustrates another two-piece implementation PI 100", where a distal lens 111" is either part of a contact module 120" or can be inserted into the contact module 120". This PI 100" can be completed by again docking the contact module 120" to the eye, attaching an attachment module 110" to an ophthalmic system 10", aligning the two and gently lowering the attachment module 110" onto the contact module 120" so that a receiving rim 113" of the attachment module 110" makes contact with a contact rim 126" of the contact module 120". After the contact was completed and a sufficient seal has been established, a viscoelastic substance 121" can be provided e.g. through an input port 122".

While the embodiments of FIG. 2 and FIG. 3 were referred to as two-piece PIs, the scope of the embodiments is broader and includes all multi-piece PIs that have two or more components or modules. These multiple components can be connectable to form an attachment module, a contact module, or additional modules with additional functionalities.

Of course, as in all medical processes, providing and securing a sterile environment for the patient is of paramount importance. This requirement can be satisfied by some embodiments of the patient interface 100, or one of its components, being disposable. In other embodiments, where the patient interface 100 or one of its components is reusable, this can be achieved e.g. by the PI 100 being sterilizable.

One reason why implementations of the patient interface 100 can keep the deformation of the cornea lower than previous systems is that they are adaptive. The surface that contacts the eye is not a rigid, or hard lens, but a deformable, soft surface. Thus, after docking the contact module 120 to the eye and introducing the viscoelastic substance 121, the radius of the contact surface, formed by the viscoelastic substance, can adapt to the radius of the cornea.

As pointed out above, even rigid contact lenses can limit the deformation of a particular cornea to a minimal degree, or even to zero. However, the corneal radius of curvature varies from patient to patient. Thus, rigid-lens systems cannot minimize the corneal deformation for a group of patients.

In contrast, the above-described patient interfaces with adaptive, or deformable, contact surfaces can minimize the corneal deformation of a group of patients with varying corneal radii. One way to capture this fact is that if the contact module 120 of the PI 100 is attached to a first eye with an apical corneal radius of R1 and causes a $\delta R1$ change of this corneal radius, and separately, it is attached to a second eye with an apical corneal radius of R2, and causes a $\delta R2$ change of that corneal radius, then the contact module 120 is capable of limiting $\delta R1$ and $\delta R2$ to be less than $0.5*|R1-R2|$, the lowest value a rigid contact lens could achieve as a joint limit for both radius changes. Implementations of the adaptive PIs can satisfy this condition in relation apical corneal radii R1 and R2 in the range typical for human eyes, between 7.5 mm and 8.2 mm. In some other implementations, the PI 100 can limit $\delta R1$ and $\delta R2$ to be less than $0.25*|R1-R2|$.

Figure 4:
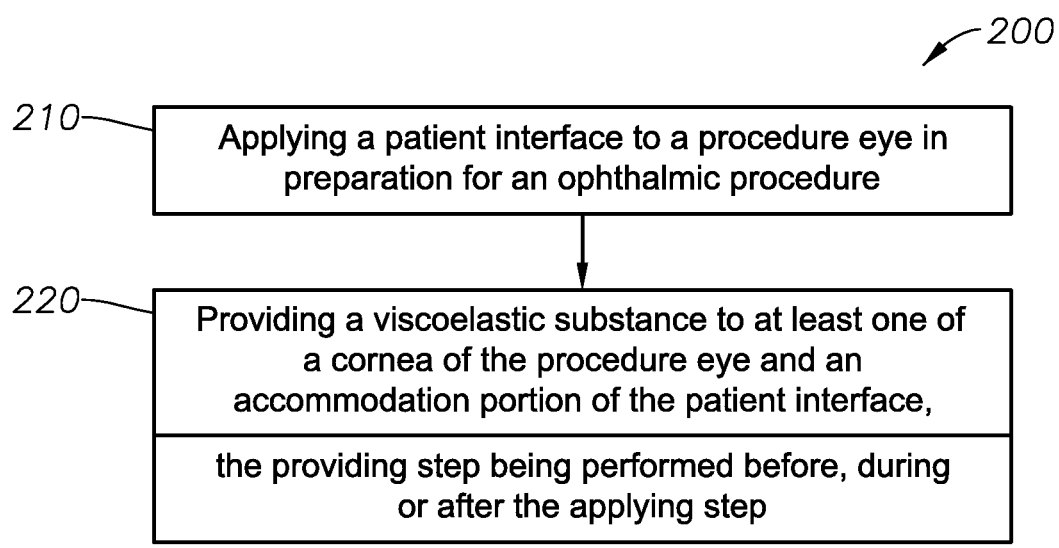
FIG. 4 illustrates a method of utilizing a patient interface.

FIG. 4 illustrates a method 200 of utilizing the patient interface 100 for an ophthalmic procedure. The method 200 can include the following:

210—applying the patient interface to a procedure eye in preparation for the ophthalmic procedure; and 220—providing a viscoelastic substance to at least one of a cornea of the procedure eye and an accommodation portion of the patient interface, wherein the providing is performed before, during or after the applying.

The step 210 can include aligning a one-piece patient interface 100 with an optical axis of the eye, followed by lowering and docking the patient interface 100 to the eye. After docking, the eye can be held steady by applying at least a partial vacuum to a suction subsystem of the patient interface 100. As mentioned before, two-piece patient interfaces 100' and 100" can be applied to the eye by attaching the attachment module 110'/110" to the distal end of the ophthalmic system 10'/10", docking the contact module 120'/120" to the eye, aligning the attachment module 110'/110" and the contact module 120'/120", and finally lowering the attachment module 110'/110" to dock it to the contact module 120'/120". Again, the application of a partial vacuum can be used to hold the eye steady.

For either one-piece or two-piece interfaces, the providing step 220 can include introducing the viscoelastic substance 121/121'/121" into the accommodation space 123/123'/123". As before, the viscoelastic substance 121/121'/121" can include a fluid, a liquid, a gel, a cream, an artificial tear, a film, an elastic material, or a viscous material.

In the method 200, the ophthalmic procedure can be an imaging procedure, a diagnostic procedure, a laser-assisted procedure, or an ophthalmic surgical procedure.

Figure 5A:
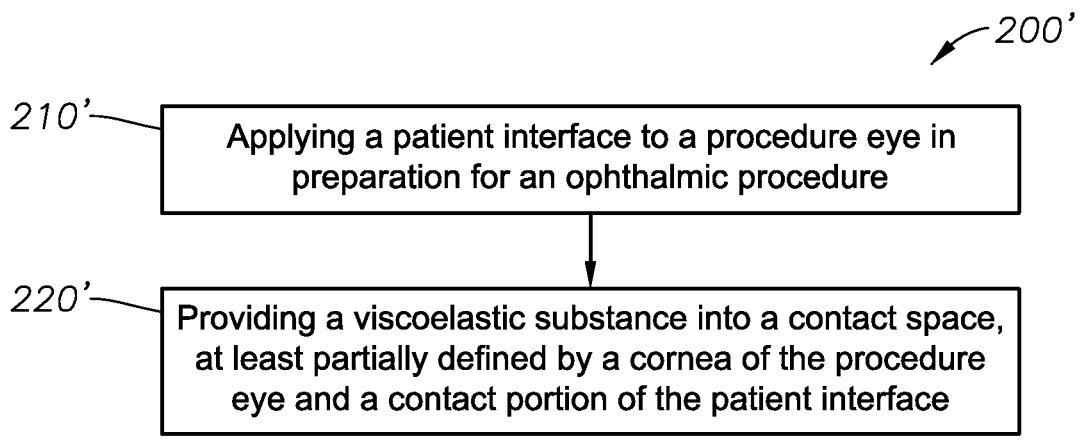
FIGS. 5A-B illustrate different sequences of the method of FIG. 4.

FIG. 5A illustrates that a providing step 220' can be performed after an applying step 210'.

Figure 5B:
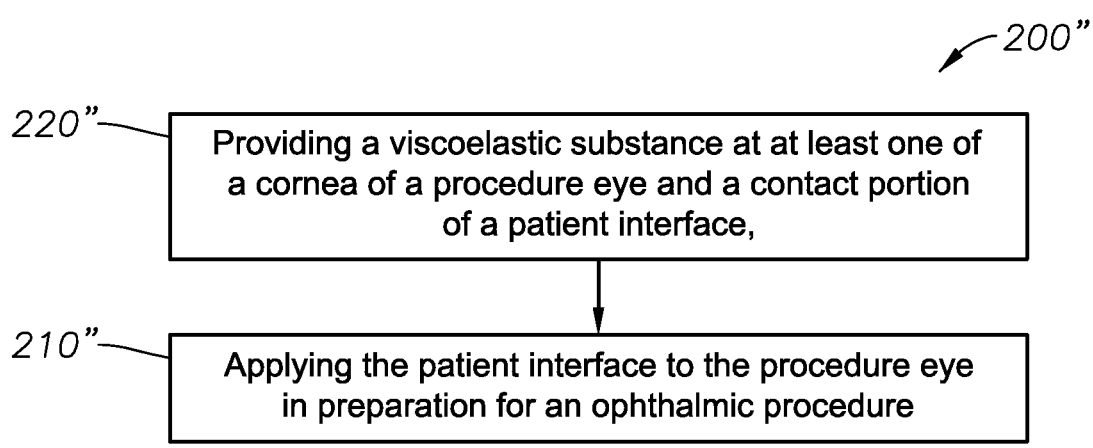

FIG. 5B illustrates that a providing step 220" can be performed before an applying step 210". In some cases, the providing step 220 and the applying step 210 can be performed in a partially overlapping manner.

FIGS. 6A-H illustrate that in various implementations the viscoelastic substance can be provided in several different manners. Elements analogous to the elements in earlier embodiments will not be expressly described and at some places will even be omitted for clarity. Nevertheless, combinations with the analogous elements from FIGS. 1-5 are all within the scope of the invention.

FIGS. 6A-E illustrate various step-sequences for one-piece integrated patient interfaces.

Figure 6A:
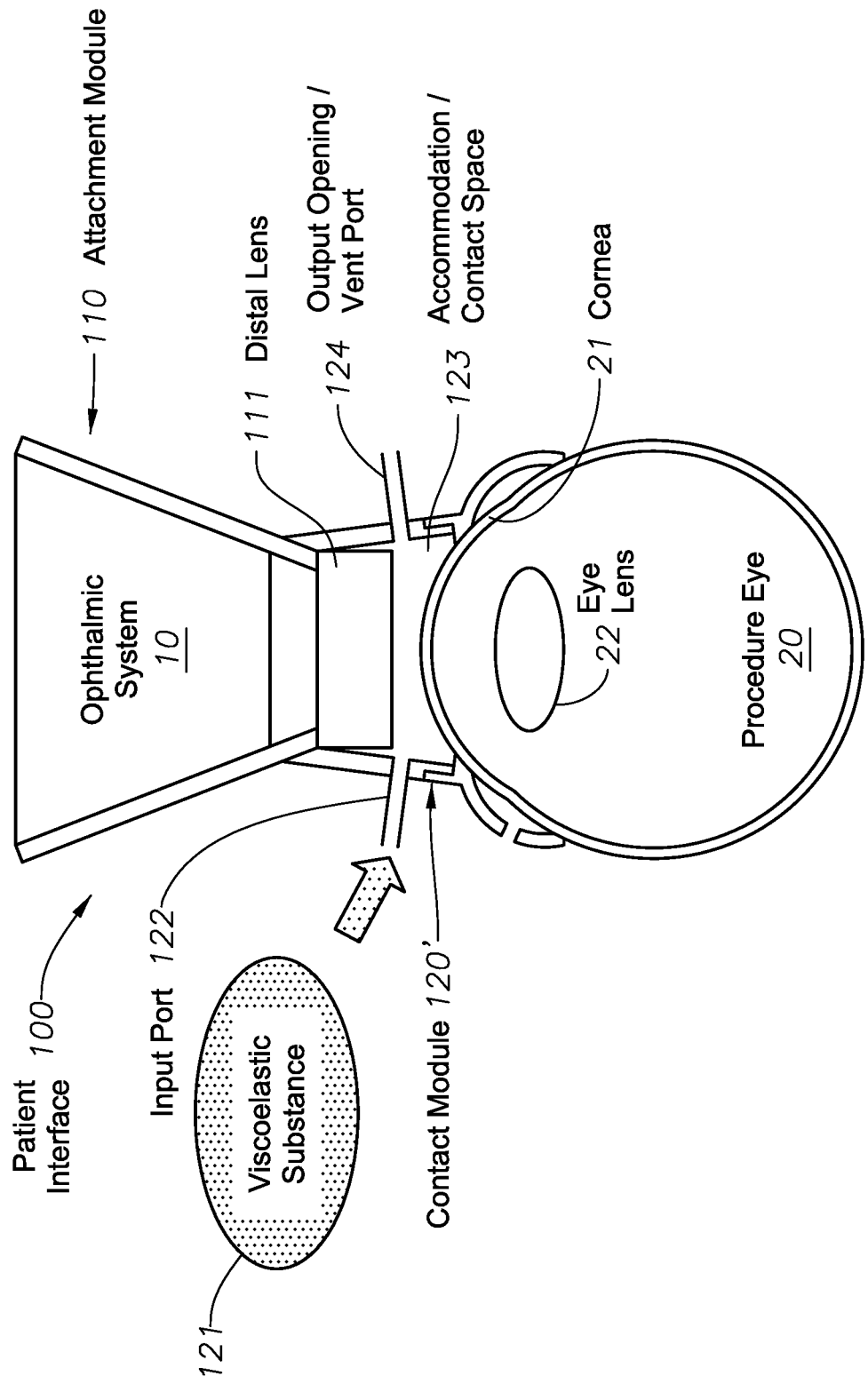
FIGS. 6A-H illustrate various implementations of providing a viscoelastic substance for the ophthalmic procedure.

FIG. 6A illustrates that the providing step 220 can include providing the viscoelastic substance 121 through the input port 122 of the patient interface into the contact space 123, where the contact space 123 is at least partially bordered by the patient interface and the procedure eye, after the applying step 210. Here and in subsequent implementations, the viscoelastic substance 121 can be provided e.g. by using a syringe, or any other suitable applicator.

Figure 6B:
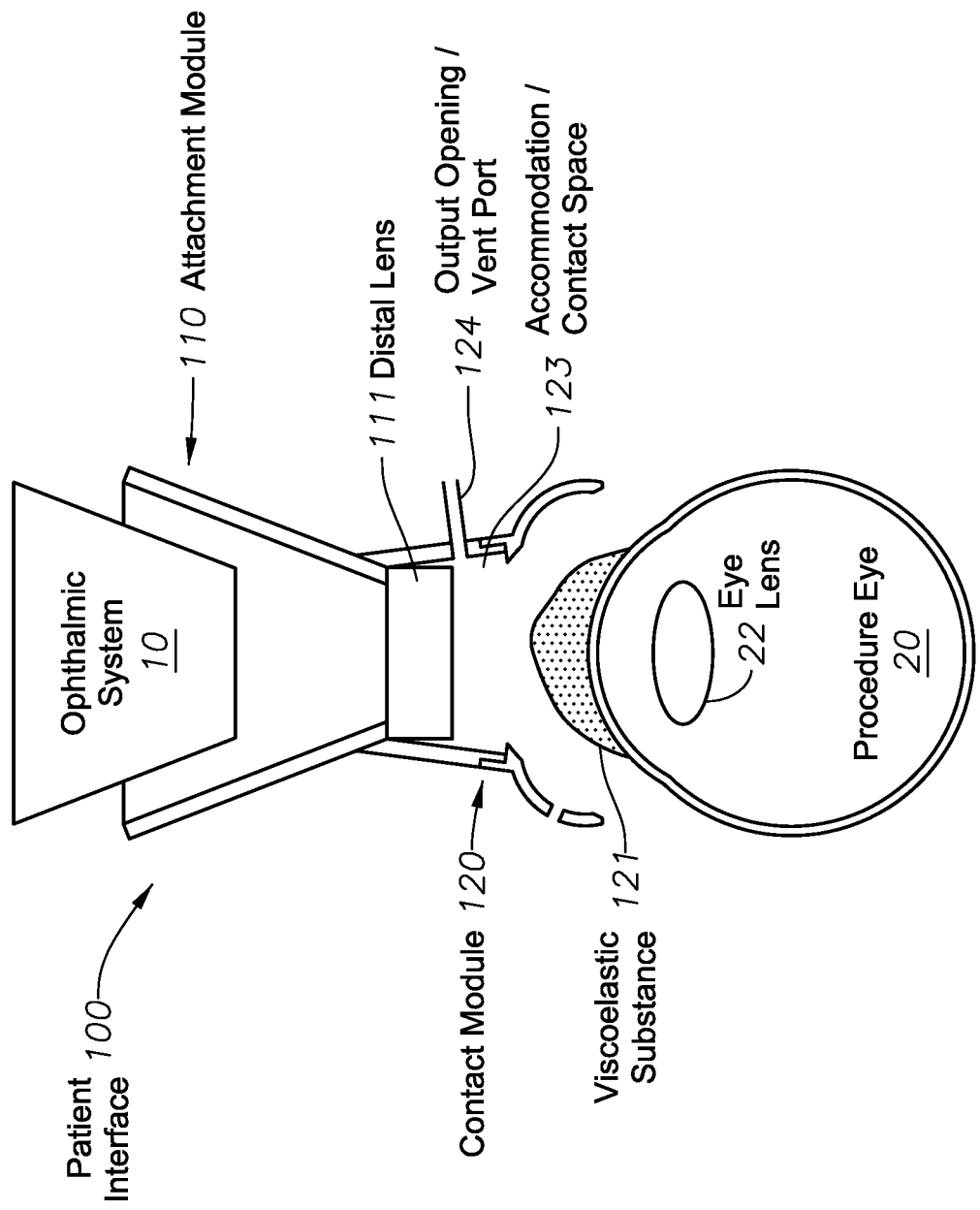

FIG. 6B illustrates that in some implementations of the providing step 220, the viscoelastic substance 121 can be provided onto the cornea of the procedure eye before the patient interface is docked to the cornea. Again, a wide variety of applicators can be used, including syringes.

Figure 6C:
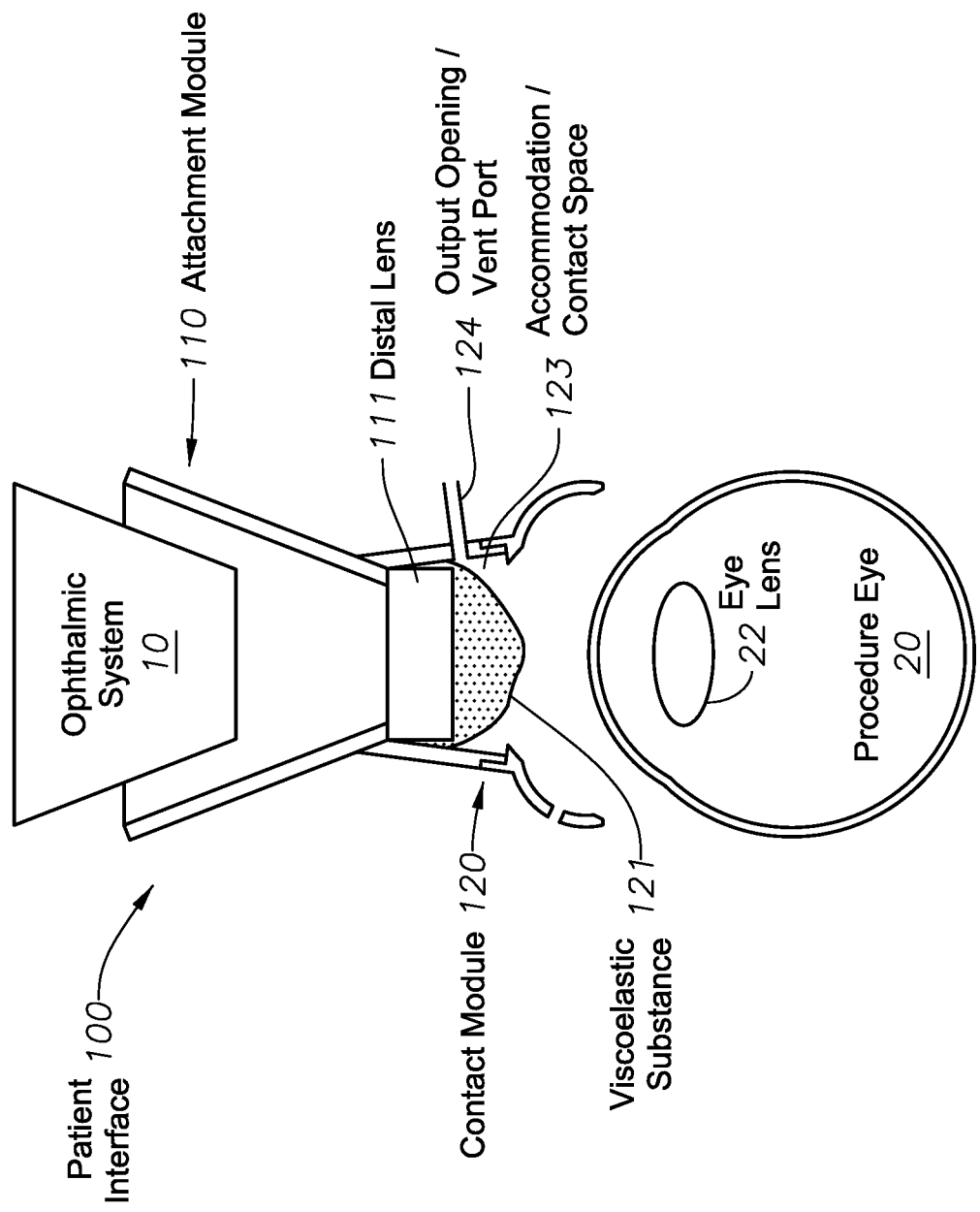

FIG. 6C illustrates that in some implementations of the providing step 220, the viscoelastic substance 121 can be provided at the contact module or portion 120 of the patient interface before the applying step 210. The viscoelastic substance 121 can be introduced, for example, by a wide variety of applicators, including syringes. In other cases, the viscoelastic substance 121 can be disposed in the patient interface 100 by its manufacturer, affixed to the PI 100 with e.g. a cover sheet or foil that can be removed by the surgeon to expose and provide the gel or cream of the viscoelastic substance 121.

The injection of certain viscoelastic substances 121, e.g. with a syringe, may lead to the formation of a large number of microscopic bubbles in the injected gel or fluid. Many of these microscopic bubbles can have diameters comparable to the operational wavelength of the laser or light beam, and thus can scatter the beam intensely. For this reason, the bubbles can lead to a pronounced deterioration of the optical performance of the system.

Figure 6D:
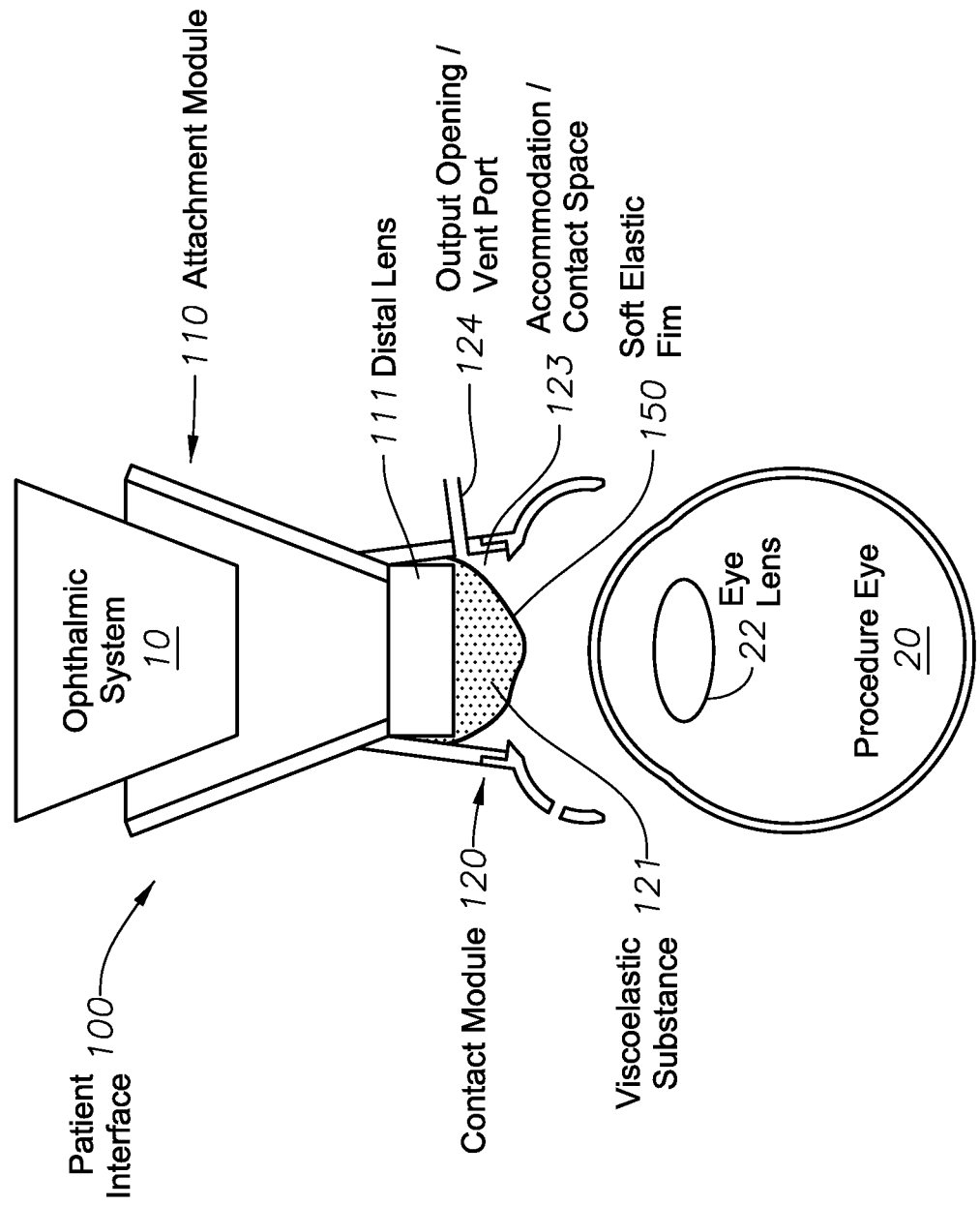

FIG. 6D illustrates that in some embodiments the formation of bubbles can be preempted by providing the viscoelastic substance 121 contained with or within a soft elastic film or membrane 150. In a preparatory step, the fluid or gel inside the soft elastic film 150 can be carefully de-gassed and then the film 150 sealed airtight to prevent the formation of bubbles. When the patient interface is docked on the cornea, the soft elastic film 150 is not removed, thus preventing the formation of the microscopic bubbles. Since the membrane 150 is soft and elastic, it still allows the extensive adaptation of the viscoelastic substance 121 to conform to the curvature of the cornea and thus minimize its deformation.

Additionally, bubbles may be generated at the contact surface where the viscoelastic substance 121 meets the cornea. Some embodiments manage these bubbles by providing the viscoelastic substance 121 with its maximum height, or apex, close to the optical axis of the ophthalmic system 10. With this design, when the PI 100 makes first contact with the viscoelastic substance 121, this contact happens at the center or optical axis. The continued lowering of the PI 100 extends the contact area moving radially outward from the center. Even if gas bubbles were trapped at the contact surface initially, this design presses and squeezes the bubbles radially outward, largely eliminating them from the path of the laser beam. This is to be contrasted with designs in which the viscoelastic substance 121 does not have the maximal height at the center. In these designs gas bubbles may remain trapped at the contact surface, leading to enhanced light scattering.

Figure 6E:
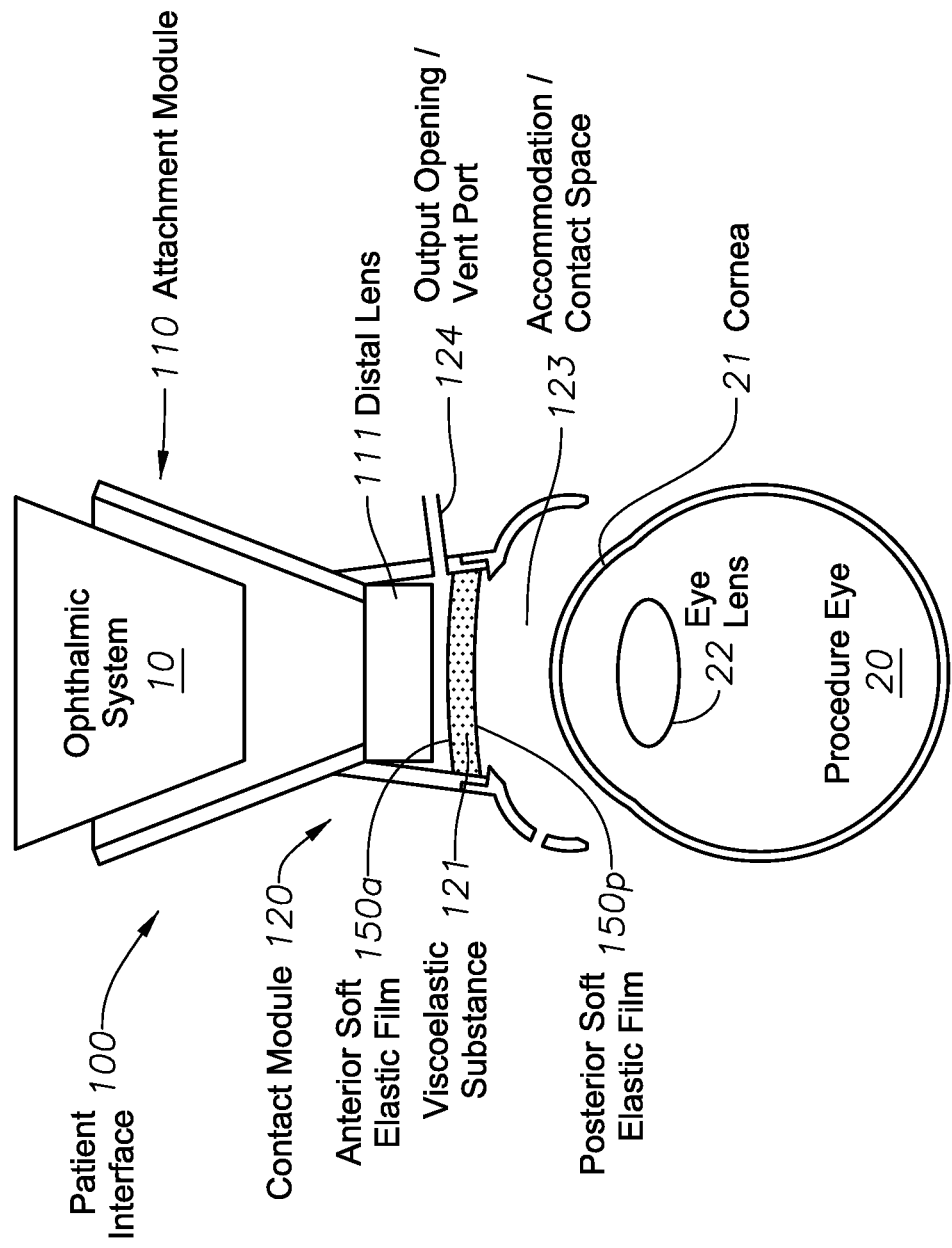

FIG. 6E illustrates an embodiment where the viscoelastic substance is provided at the contact portion 120 of an integrated one-piece patient interface 100, contained in a space defined by an anterior soft elastic film 150*a* on an anterior side and a posterior soft elastic film 150*p* on the posterior side of the viscoelastic substance 121.

This design can utilize two separate films or a single membrane completely surrounding the viscoelastic substance 121, in effect forming an elastic containment bag. Such implementations can provide additional control over the shape of the viscoelastic substance 121.

Figure 6F:
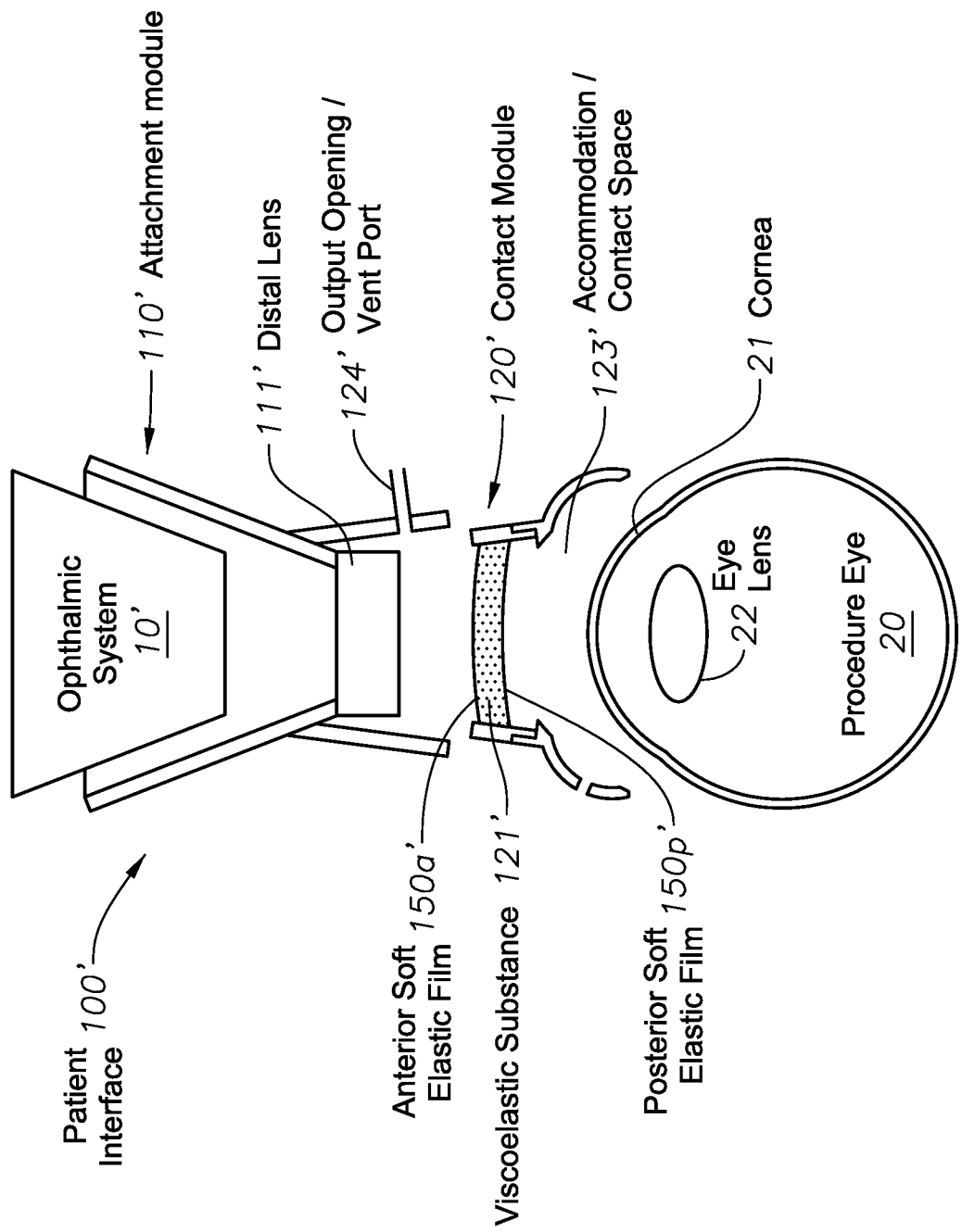

FIG. 6F illustrates a two-piece patient interface 100', where the viscoelastic substance 121' is contained between the two films 150*a* and 150*p*, or inside an elastic bag with two surfaces, at the contact module 120' before it is connected to the attachment module 110'. In this embodiment, the distal lens is part of the attachment module 110'.

Figure 6G:
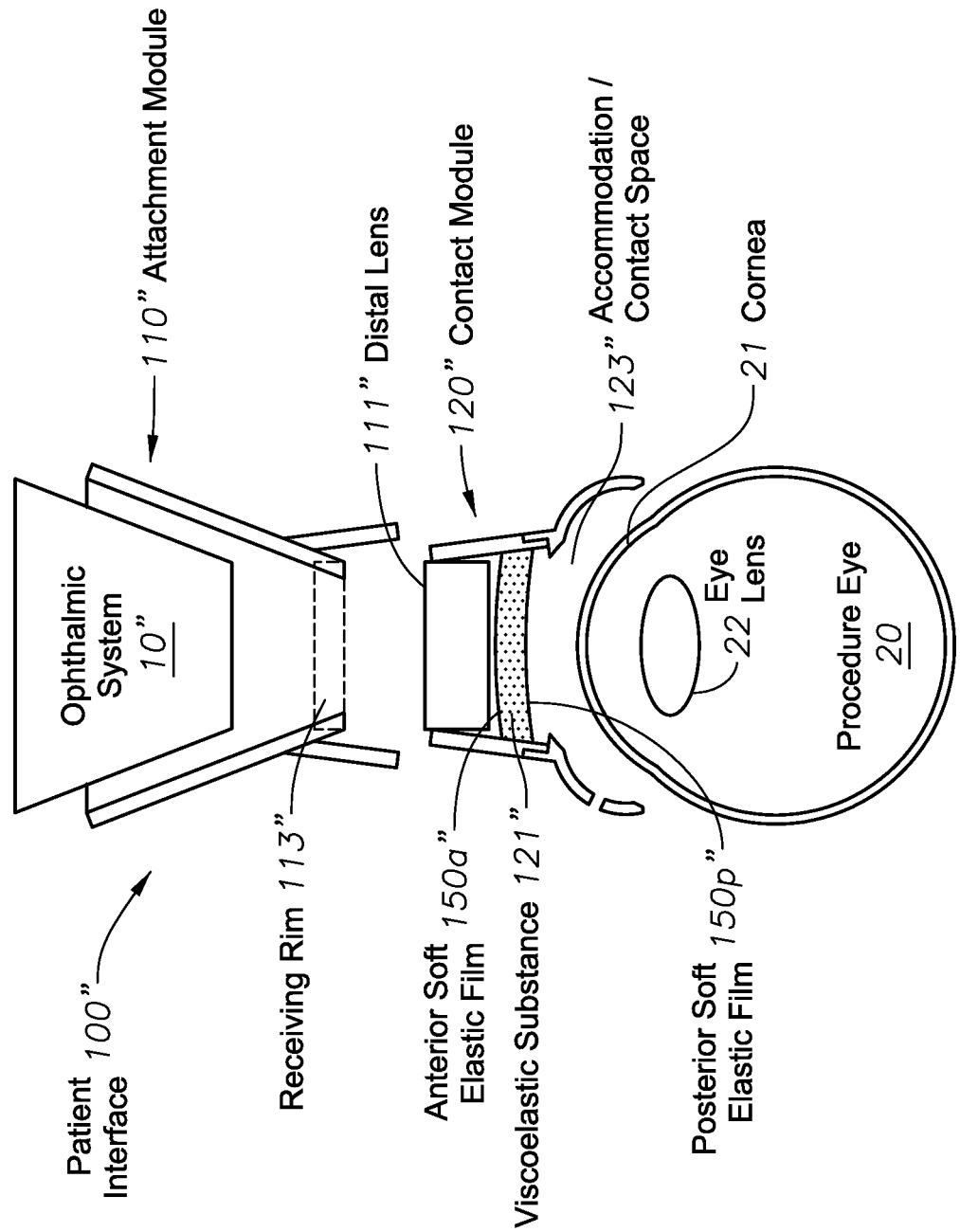

FIG. 6G illustrates a variant implementation of a two-piece patient interface 100", where the viscoelastic substance 121" is again provided in an elastic containment bag or between two soft films 150*a"* and 150*p"*. In this implementation a distal lens 111" is part of the contact module 120".

Figure 6H:
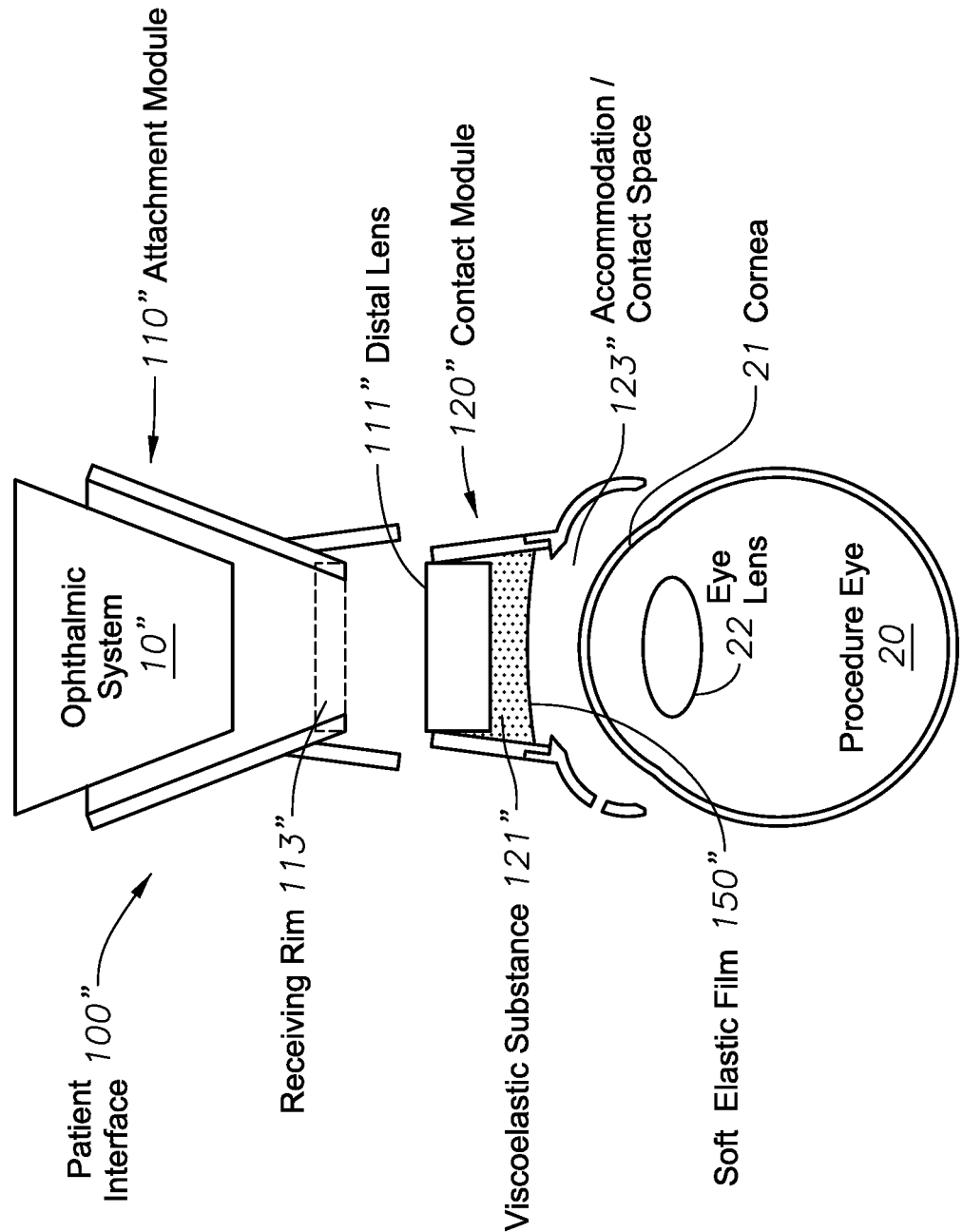

FIG. 6H illustrates yet another variant implementation, where the viscoelastic substance 121" can be provided and contained in a space at least partially defined by a soft elastic film 150" and the distal lens 111".

Some implementations can have additional modules to manage the gas or bubbles, contained either in the viscoelastic substance 121 after its injection into the accommodation space 123, or trapped at the contact surface with the patient interface 100. These additional modules can include a degassing subsystem, connectable to the patient interface and configured to degas the viscoelastic substance 121 or the contact surface. Several such degassing systems and methods are known, among them: reducing a pressure experienced by the viscoelastic substance 121, heating the viscoelastic substance 121, performing a membrane-based degasification, substituting an inert gas for the air atmosphere, manipulating a surface tension of the viscoelastic substance 121, and adding a reductant to it.

While this document contains many specifics, these should not be construed as limitations on the scope of the invention or of what may be claimed, but rather as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination. Also, variations and enhancements of the described implementations, and other implementations can be made based on what is described.

The invention claimed is:

1. A patient interface system for an ophthalmic system, comprising:
    a multi-piece patient interface, comprising
        an attachment module, attachable to the ophthalmic system;
        a contact module, configured
            to be docked to a procedure eye,
            to accommodate a viscoelastic substance in an accommodation space at least partially bordered by the contact module and by the procedure eye, and
            to get connected to the attachment module; and
        a suction ring, coupled to the contact module, connectable to a vacuum suction system to create a partial vacuum between the suction ring and the procedure eye to reduce a mobility of the procedure eye for an ophthalmic procedure; and
    a degassing subsystem, coupled to the patient interface, comprising at least one of a pressure-reduction system, a heating system, a membrane degasification system, an inert gas substitution system, a surface tension manipulating system, and a reductant-adding system.

2. The patient interface system of claim 1, wherein:
the accommodated viscoelastic substance comprises at least one of
a fluid, a liquid, a gel, a cream, an artificial tear, a film, an elastic material, and a viscous material.

3. The patient interface system of claim 1, wherein:
the accommodated viscoelastic substance has a refractive index closer to a refractive index of a cornea of the procedure eye than to a refractive index of air at an operating wavelength of the ophthalmic system.

4. The patient interface system of claim 1, wherein:
the accommodated viscoelastic substance has a refractive index within a range of 1.24-1.52 at an operating wavelength of the ophthalmic system.

5. The patient interface system of claim 1, wherein:
the accommodated viscoelastic substance has a refractive index within a range of 1.35-1.41 at an operating wavelength of the ophthalmic system.

6. The patient interface system of claim 1, wherein:
a component of the patient interface is at least one of disposable, sterilizable, and reusable.

7. The patient interface system of claim 1, wherein:
the contact module is configured to accommodate the viscoelastic substance after the contact module has been docked to the procedure eye.

8. The patient interface system of claim 1, wherein:
the contact module is configured to accommodate the viscoelastic substance being introduced into the accommodation space.

9. The patient interface system of claim 8, the patient interface comprising:
one or more input ports to introduce the viscoelastic substance into the accommodation space.

10. The patient interface system of claim 1, the patient interface comprising:
one or more output openings configured to enable a discharge of at least one of air, gas, and the viscoelastic substance from the accommodation space.

11. The patient interface system of claim 1, the patient interface comprising:
a vent port, configured to couple the contact module to the degassing subsystem.

12. The patient interface system of claim 1, wherein:
the suction ring is coupled to the contact module through a suction port; and
the degassing subsystem is coupled to the contact module through an output port.

13. The patient interface system of claim 1, wherein:
the contact module is configured to accommodate the viscoelastic substance before getting connected to the attachment module.

14. The patient interface system of claim 1, wherein:
the multi-piece patient interface is a two-piece patient interface, comprising the attachment module and the contact module.

15. The patient interface system of claim 1, the attachment module comprising:
a distal lens.

16. The patient interface of claim 15, wherein:
the patient interface is configured so that the distal lens does not contact the cornea of the procedure eye after the contact module was docked to the procedure eye and the attachment module was connected to the contact module.

17. The patient interface system of claim 1, wherein:
the patient interface is configured to keep a change of an apical curvature of a cornea of the procedure eye below 10% upon an attachment of the patient interface to the procedure eye.

18. The patient interface system of claim 17, wherein:
the patient interface is configured to keep a change of the apical curvature of the cornea of the procedure eye below 3% upon the attachment of the patient interface to the procedure eye.

19. The patient interface system of claim 1, the ophthalmic system comprising at least one of:
an imaging system;
a diagnostic system; and
an ophthalmic surgical laser system.

20. The patient interface system of claim 1, the suction ring comprising:
more than one suction chamber.

* * * * *